United States Patent [19]
Gregory

[11] Patent Number: 5,836,940
[45] Date of Patent: Nov. 17, 1998

[54] PHOTOACOUSTIC DRUG DELIVERY

[75] Inventor: Kenton W. Gregory, Portland, Oreg.

[73] Assignee: Latis, Inc., West Conshohocken, Pa.

[21] Appl. No.: 644,533

[22] Filed: May 10, 1996

Related U.S. Application Data

[63] Continuation-in-part of Ser. No. 328,857, Oct. 25, 1994, Pat. No. 5,571,151.

[51] Int. Cl.$^6$ ..................................................... A61B 17/36
[52] U.S. Cl. .................................. 606/15; 606/9; 606/16; 607/89; 604/20
[58] Field of Search .................................... 606/7, 15, 16, 606/9; 607/88, 89; 604/20–22

[56] References Cited

U.S. PATENT DOCUMENTS

| | | |
|---|---|---|
| 3,858,577 | 1/1975 | Bass et al. . |
| 3,995,934 | 12/1976 | Nath . |
| 4,011,403 | 3/1977 | Epstein et al. . |
| 4,045,119 | 8/1977 | Eastgate . |
| 4,201,446 | 5/1980 | Geddes et al. . |
| 4,313,431 | 2/1982 | Frank . |
| 4,445,892 | 5/1984 | Hussein et al. . |
| 4,576,177 | 3/1986 | Webster, Jr. ................................ 606/15 |
| 4,641,912 | 2/1987 | Goldenberg . |
| 4,697,870 | 10/1987 | Richards . |
| 4,729,373 | 3/1988 | Peyman ................................. 128/303.1 |
| 4,848,336 | 7/1989 | Fox et al. . |
| 4,862,886 | 9/1989 | Clarke et al. .......................... 128/303.1 |
| 4,870,953 | 10/1989 | DonMichael ........................... 128/24 A |
| 4,875,897 | 10/1989 | Lee . |
| 4,927,231 | 5/1990 | Levatter . |
| 4,976,710 | 12/1990 | Mackin . |
| 5,053,033 | 10/1991 | Clarke . |
| 5,169,396 | 12/1992 | Dowlatshahi et al. . |
| 5,187,572 | 2/1993 | Nakamura et al. . |
| 5,188,632 | 2/1993 | Goldenberg . |
| 5,217,454 | 6/1993 | Khoury . |

(List continued on next page.)

FOREIGN PATENT DOCUMENTS 87304072.9  12/1987  European Pat. Off. .

OTHER PUBLICATIONS

Gregory, Kenton W. and Anderson, R. Rox, "Light Core Light Guide for Laser Angioplasty," *IEEE Journal of Quantum Electronics*, vol. 26, No. 12, pp. 2289–2296, Dec. 1990.
Shangguan, Hanqun; Casperson, Lee W.; Shearin, Alan; Gregory, Kenton, and Prahl, Scott A., *Photoacoustic Drug Delivery: The Effect of Laser Parameters on Spatial Distribution of Delivered Drug*, SPIE vol. 2391, May 25, 1995, pp. 394–402.

*Primary Examiner*—Robert L. Nasser
*Attorney, Agent, or Firm*—Marger, Johnson, McCollom & Stolowitz PC

[57] ABSTRACT

A method and apparatus for locally delivering an active agent to a selected site in a body lumen using a liquid core laser catheter having a flexible tube for insertion into the lumen, a conduit housed within the tube for coupling a flow of light transmissive liquid from an external source to the site, and an optical fiber housed within the tube for coupling laser energy from an external source to the site. In one embodiment, the conduit has a sidewall capable of internally reflecting light into the liquid in the conduit so that the liquid waveguides the laser energy through the conduit to the site. The method comprises preparing a solution of the active agent, the solution being optically transparent to the laser energy, inserting the flexible tube into the lumen, directing the flexible tube to the site, flowing the light transmissive liquid through the conduit, deflecting the flow of liquid to the selected site, introducing and admixing a flow of the active agent solution into the flowing liquid, and thereafter, transmitting laser energy from an external source to the site, with an amplitude sufficient to create rapid displacement of the flowing liquid thereby producing a hydraulic wave which drives the active agent into the site. In another embodiment, an optical fiber within the conduit transfers laser energy to the distal tip of the catheter whereupon it impacts and is absorbed by light absorptive liquid flowed through the conduit, thereby creating a hydraulic wave adjacent the optical fiber tip.

36 Claims, 5 Drawing Sheets

U.S. PATENT DOCUMENTS

| | | | |
|---|---|---|---|
| 5,246,436 | 9/1993 | Rowe | 606/13 |
| 5,246,437 | 9/1993 | Abela . | |
| 5,257,970 | 11/1993 | Dougherty | 604/20 |
| 5,286,254 | 2/1994 | Shapland | 604/21 |
| 5,304,171 | 4/1994 | Gregory et al. . | |
| 5,308,348 | 5/1994 | Balaban | 604/892.1 |
| 5,323,769 | 6/1994 | Bommannan | 601/604.2 |
| 5,362,309 | 11/1994 | Carter | 604/22 |
| 5,472,441 | 12/1995 | Edwards et al. | 604/21 |
| 5,501,662 | 3/1996 | Hofmann | 604/20 |
| 5,586,982 | 12/1996 | Abela | 606/15 |
| 5,632,739 | 5/1997 | Anderson et al. | 606/15 |

PHOTOACOUSTIC DRUG DELIVERY

This application is a continuation-in-part of U.S. Ser. No. 08/328,857, filed Oct. 25, 1994, now U.S. Pat. No. 5,571,151.

BACKGROUND OF THE INVENTION

1. Field of the Invention

The present invention relates to a method and apparatus for localized delivery of drugs or other active agents, and more particularly, to an apparatus and method for selectively and locally delivering an active agent to internal body tissue. More specific applications of the present invention relate to a method and apparatus for localized treating of vascular thrombosis disorders, atherogenesis, and tumors.

2. Description of Prior Art

Many techniques currently exist for delivering drugs and other active agents to body tissue. These include: oral administration, direct injection into body tissue, and intravenous administration which involves introducing the active agent directly into the blood stream. These delivery mechanisms are systemic, in that they deliver the active agent via the bloodstream throughout the entire body. Effective pharmacologic or drug therapy requires achieving adequate concentrations of an active drug at the site of desired treatment without producing concentrations of the drug elsewhere in the body that create unwanted or dangerous side-effects.

Workers in the field have discovered that many effective drugs which are capable of treating or curing disease cannot be effectively delivered systemically because the concentrations necessary for effective treatment produce adverse side-effects in other parts of the body. For example, in the case of arterial and venous thrombosis, workers in the field have identified many potent agents which are capable of degrading thrombi, but clinical application of these agents has been limited by bleeding complications which result in substantially increased morbidity and mortality. Moreover, even clinically approved agents such as streptokinase, urokinase, recombinant tissue plasminogen activators or even heparin have limited efficacy in treating acute myocardial infarction and other thrombotic disorders because they can produce systemic bleeding complications.

One approach to reducing systemic side-effects is to introduce a catheter percutaneously, through the skin, near the thrombotic site under fluoroscopic guidance. The active agent is then infused in high concentrations and flowed by the thrombus. There are, however, practical limits to the duration of such treatment. Prolonged infusion will eventually produce a total accumulated systemic dose of the agent sufficient to create adverse side-effects. In addition to the great cost of such an infusion, the prolonged indwelling of the catheter increases morbidity. The ability to administer an active agent locally to the thrombotic site without systemically affecting other tissues or creating complications, would greatly enhance the ability to effectively treat arterial and venous thrombus.

Another application for delivering an active agent to an internal body tissue is in treating cancerous tumors. The objective of such treatment is to concentrate as much of the cancer drug in the tumor as possible. Typically, workers in the field administer cancer drugs systemically through the blood stream and then use various means to localize the drug in the cancerous tumor. Nevertheless, amounts of the drug still circulate through the blood stream in sufficient concentrations to produce adverse side-effects and therefore limit the dosages of the drug which can be safely administered.

Accordingly, a need remains for a method and apparatus for locally delivering an active agent to internal body tissue. There is a further need for such an apparatus and method for treating atherosclerosis, cancerous tumors, and other internal body tissue.

SUMMARY OF THE INVENTION

The invention provides a method and apparatus for locally delivering an active agent to a selected site in a body lumen. The apparatus includes a source of the active agent, a flexible tube having a distal end for insertion into the lumen, a conduit housed in the flexible tube coupled to the source of the active agent for delivering the active agent to the site, and means for transmitting energy to the site in a pulse of sufficient amplitude to create rapid displacement of ambient body fluid thereby producing a hydraulic or pressure wave which drives the active agent into the selected site.

Another aspect of the invention is a method of locally delivering an active agent to a selected site in a body lumen containing an ambient body fluid using the above described apparatus. The method includes preparing a solution of the active agent, inserting the flexible distal end into the lumen, directing the flexible distal end to the selected site, introducing a flow of the active agent solution into the conduit for discharge at the distal end into the lumen adjacent the site and transmitting a pulse of energy from an energy generating source to the site via the catheter, with the pulse having an amplitude sufficient to create rapid displacement of the ambient fluid thereby producing a hydraulic or pressure wave which drives the active agent into the site.

In a preferred embodiment, the apparatus includes a liquid core laser catheter, for use in a drug delivery system comprising a source of an active agent in an optically transparent solution, a source of light transmissive liquid and a source of laser energy. The catheter comprises a flexible tube having a distal end for insertion into the lumen, a conduit housed within the tube, means for coupling a flow of the light transmissive liquid into the conduit, means of admixing a flow of the active agent solution into the flow of the light transmissive liquid, and means for transmitting laser energy from the energy source into the conduit. The conduit has a sidewall capable of reflecting light into the liquid in the conduit so that the liquid waveguides the laser energy through the conduit to the selected site, the energy being transmitted in a pulse of sufficient amplitude to create rapid displacement of the flowing liquid thereby producing a hydraulic or pressure wave which drives the active agent into the selected site.

Another aspect of the present invention is a method for locally delivering a drug during angioplasty using the above-described liquid core laser catheter. The method comprises preparing a solution of the active agent, the solution being optically transparent to the laser energy, inserting the flexible tube into the lumen, directing the flexible tube to the site, flowing the light transmissive liquid through the conduit, introducing and admixing a flow of the active agent solution into the flowing liquid, and thereafter, transmitting laser energy from an external source to the site, with an amplitude sufficient to create rapid displacement of the flowing liquid thereby producing a hydraulic or pressure wave which drives the active agent into the site.

In an alternate aspect of the preferred embodiment, the catheter includes an optical fiber coupled to the source of laser energy and having a terminal end adjacent the distal end of the catheter. A light absorptive liquid is flowed through the conduit around the optical fiber so that it is discharged from the distal end of the catheter adjacent the selected site. Laser energy flowing through the optical fiber emerges from the terminal end of the fiber into the light absorptive liquid and creates a rapid displacement of the flowing liquid thereby producing a hydraulic or pressure wave which drives the active agent into the selected site. The distal end of the catheter is preferably positioned from a point immediately adjacent to the site or upto to 10 millimeters from the selected site.

Characteristics of the transmitted laser energy which have been found to alter the effectiveness of the localized drug delivery are the tissue strength of the target material and surrounding material, the laser energy, the absorption coefficient of the target tissue, the cross-sectional area of the laser energy transmissive means and the number of laser energy pulses used.

The foregoing and other objects, features and advantages of the invention will become more readily apparent from the following detailed description of a preferred embodiment of the invention which proceeds with reference to the accompanying drawings.

DESCRIPTION OF THE ILLUSTRATED EMBODIMENTS

In the following description of illustrated embodiments of the invention, I now describe a system for locally delivering an active agent to a site in a body lumen. Those skilled in the art will appreciate that the invention has particular utility in ablating obstructions in the cardiovascular system such as atheromatous plaque, an atheroembolus, thrombus, and blood clots. In addition, in its broader aspects, the invention has utility in medically treating tumors, lesions, kidney stones, gall stones, polyps, and the like.

Figures 1, 2:
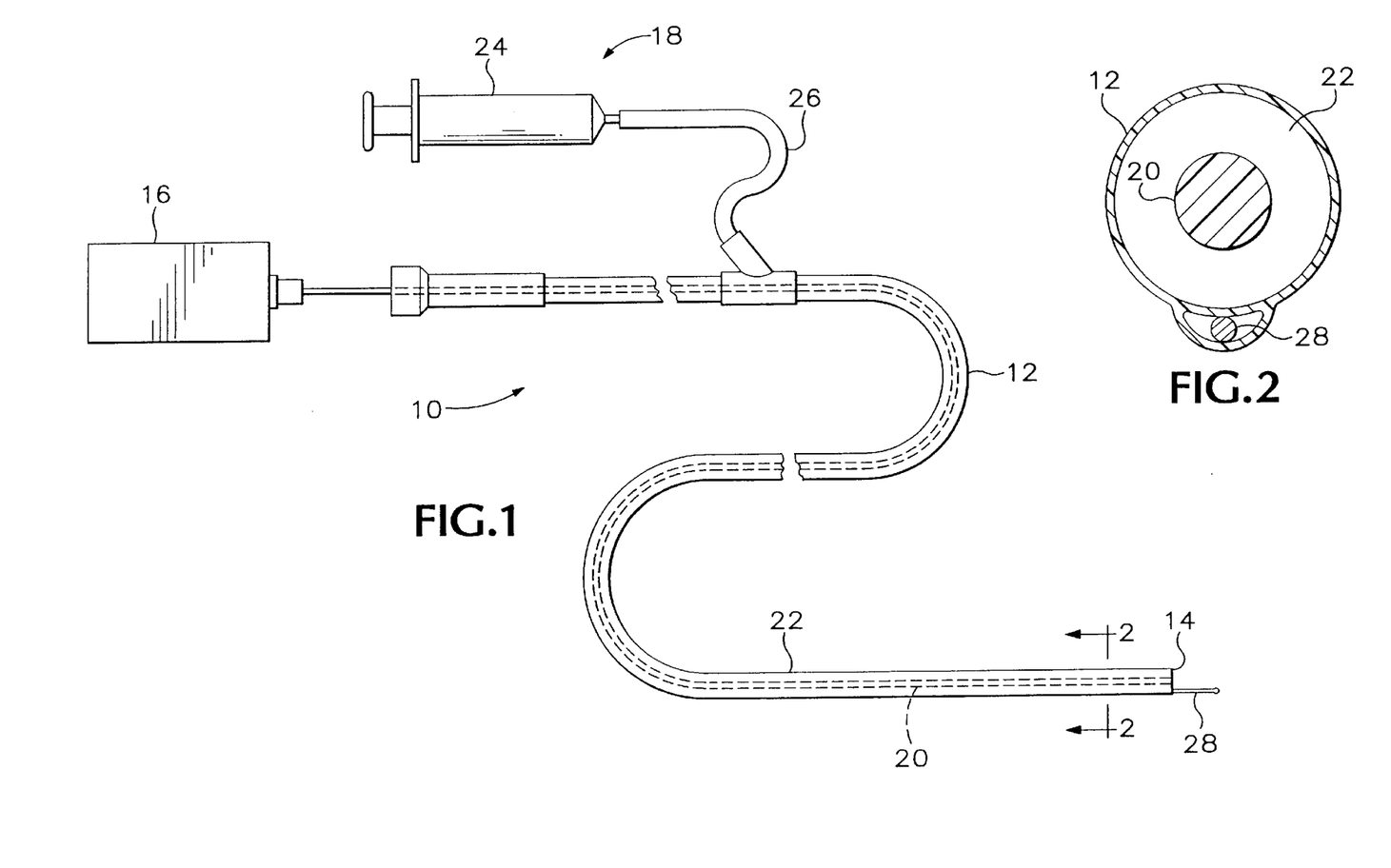
FIG. 1 is a schematic diagram of the photoacoustic drug delivery system according to the present invention.
FIG. 2 is a cross-sectional view taken along lines 2—2 of FIG. 1.

FIG. 1 illustrates a drug delivery system 10 of the present invention, shown in schematic form. System 10 must be capable of delivering an active agent within a body lumen to the site to be treated. In addition, system 10 must be capable of transmitting a pulse of energy to the site which is of sufficient amplitude to create a hydraulic or pressure wave proximate to the selected site contained in the lumen which in turn drives the active agent into the site.

In general terms, system 10 comprises a tube or catheter 12 having a flexible distal end 14 for insertion into the lumen, an external source 16 of energy, and an external source 18 of the active agent. Catheter 12 includes any medical device designed for insertion into a body lumen to permit injection of fluids, to keep the body lumen open, or for any other purpose. The present invention has applicability for use within any body lumen including, among others, an artery, a vein, a ureter, a common bile duct, a trachea, a bronchus, a gastrointestinal tract, and the like. By way of example only, the present invention can be used for local delivery of an active agent to an atheromatous plaque, an atheroembolus, a thrombus, a blood clot, a lesion, a kidney stone, a gall stone, a tumor, and a polyp.

The particular source of energy 16 illustrated in FIG. 1 may be any source of electromagnetic energy, including radio frequency energy or ultrasound. I prefer, however, that source 16 be a source of laser energy such as a laser emitting energy in short pulses. The exact configuration, type and method of generating energy is not critical, provided that the energy is delivered in pulses having amplitudes sufficient to create vaporization of material contained in the lumen. However, certain preexisting characteristics of the target material and selectable characteristics of the laser energy pulse can improve the penetration of the agent into the tissue as shown by the experimental results detailed below. The energy generated by source 16 is transmitted to distal end 14 via energy transmitting means 20. Transmitting means 20, as illustrated in FIGS. 1 and 2, is an optical fiber having a selected diameter 21 (shown best in FIG. 3) which transmits laser energy. The output of source 16 is directed to the proximal end of optical fiber 20. The other (distal) end of fiber 20 is housed within catheter 12 which enables it to be fed through the lumen. It is assumed that a bundle of optical fibers can perform a similar task as the single fiber shown in FIGS. 1–3. The bundle can be comprised of fibers which are between 30 adn 300 micrometers in diamter. Alternatively, transmitting means 20 can be a wire for the transmission of radio frequency energy or for the transmission of ultrasound.

The active agent in solution is introduced at the proximal end of conduit 22 from the active agent source 18. The active agent solution is discharged into the conduit 22 by way of a liquid discharge means such as an injector pump or, as illustrated in FIG. 1, a syringe 24 and surgical tubing 26. The active agent can be any drug, enzyme, genetic material, or other material which can be dissolved in solution or carried in fluid (e.g. microspheres, liposomes, gold particles etc.). For example, during the treatment of blockages in the cardiovascular system, streptokinase, urokinase, recombinant tissue plasminogen activator, or heparin can be used.

Figure 3:
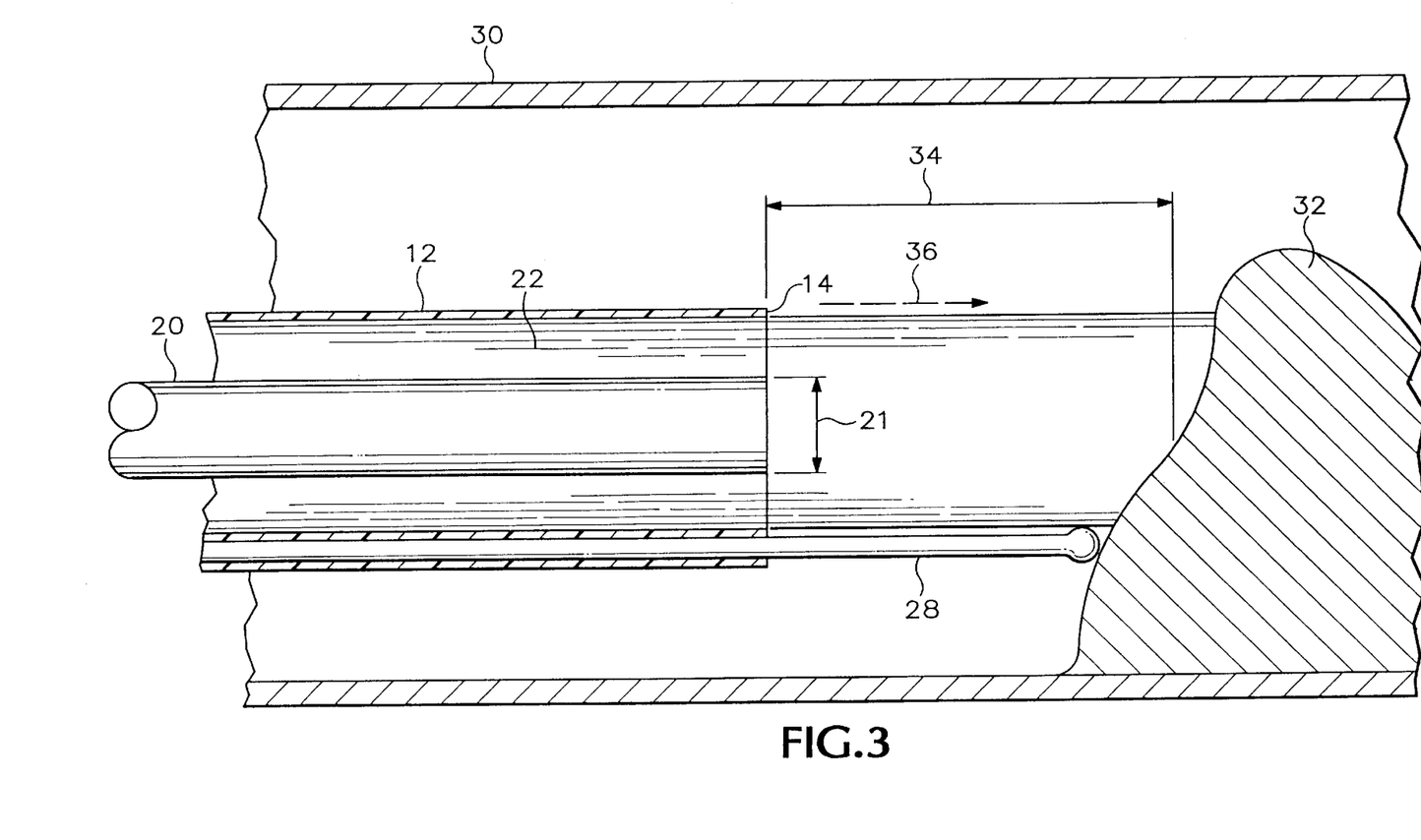
FIG. 3 is a lengthwise sectional view of the distal end portion of the system of FIG. 1, shown in an arterial lumen in proximity to a blood clot.

To practice the invention, I first prepare a solution of the active agent which I ready in syringe 24. Virtually any concentration of solution can be used depending upon the desired medical effect. Next, as illustrated in FIG. 3, I insert catheter 12 into lumen 30 and guide the catheter to the site 32 that I have selected for treatment. Preferably, I use a guidewire 28 to position the distal end 14 adjacent the selected site 32 by a selected distance 34. Once I have appropriately positioned the distal end 14 of catheter 12 adjacent to the site, I begin expelling solution from syringe 24 to introduce a flow of the active agent solution into conduit 22 for discharge at distal end 14. Though a manual hand-driven syringe can be used, the preferred method uses a mechanically driven syringe or reservoir. After I generate a flow of active agent solution, as shown by directional arrow 36, I activate the high energy laser 16. Optical fiber 20 launches the laser energy into the ambient liquid contained in lumen 30 and the flowing solution of active agent.

The pulsed laser energy creates at least two types of vapor bubbles in the liquid. One type of vapor bubbles are created by the decomposition of organic materials in the ambient body liquid into carbon dioxide ($CO_2$) and complex organic gases. In addition, the pulsed laser energy creates bubbles which result from the heating of water ($H_2O$) contained in the ambient liquid. The pulse of energy creates both of these types of bubbles very rapidly, e.g. in less than 1 milliseconds.

Figure 4A:
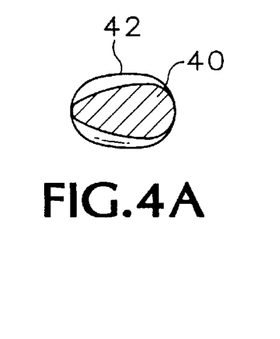
FIGS. 4A–C is a depiction of a rapidly expanding gas bubble in accordance with the present invention.
Figure 4B:
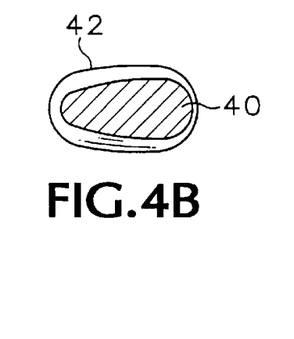
Figure 4C:
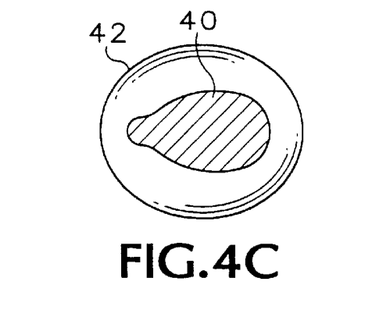

Bubble creation produces at least two effects. Initially, a pressure wave is created which precedes bubble expansion and then a hydraulic wave is created by fluid displacement from the rapidly expanding bubble. A rapidly expanding gas bubble is shown in FIGS. 4A, 4B and 4C. It is theorized that, the expanding bubble 40, produces an increased fluid pressure along the expanding pressure front 42 and an expanding hydraulic wave caused directly by the expanding surface of bubble 40. FIGS. 4A, 4B and 4C show the relative size of the bubble and pressure front formation at times of 5 nanoseconds, 12 ns and 32 ns, respectively. It has been demonstrated, for example, that laser energy absorption by blood produced rapidly expanding vapor bubbles and high-pressure transients of between 10 and 1200 atmospheres. A rapidly expanding vapor bubble can also displace local fluid containing the drug outward into the surrounding tissue without producing significant systemic concentrations.

Figures 5, 6:
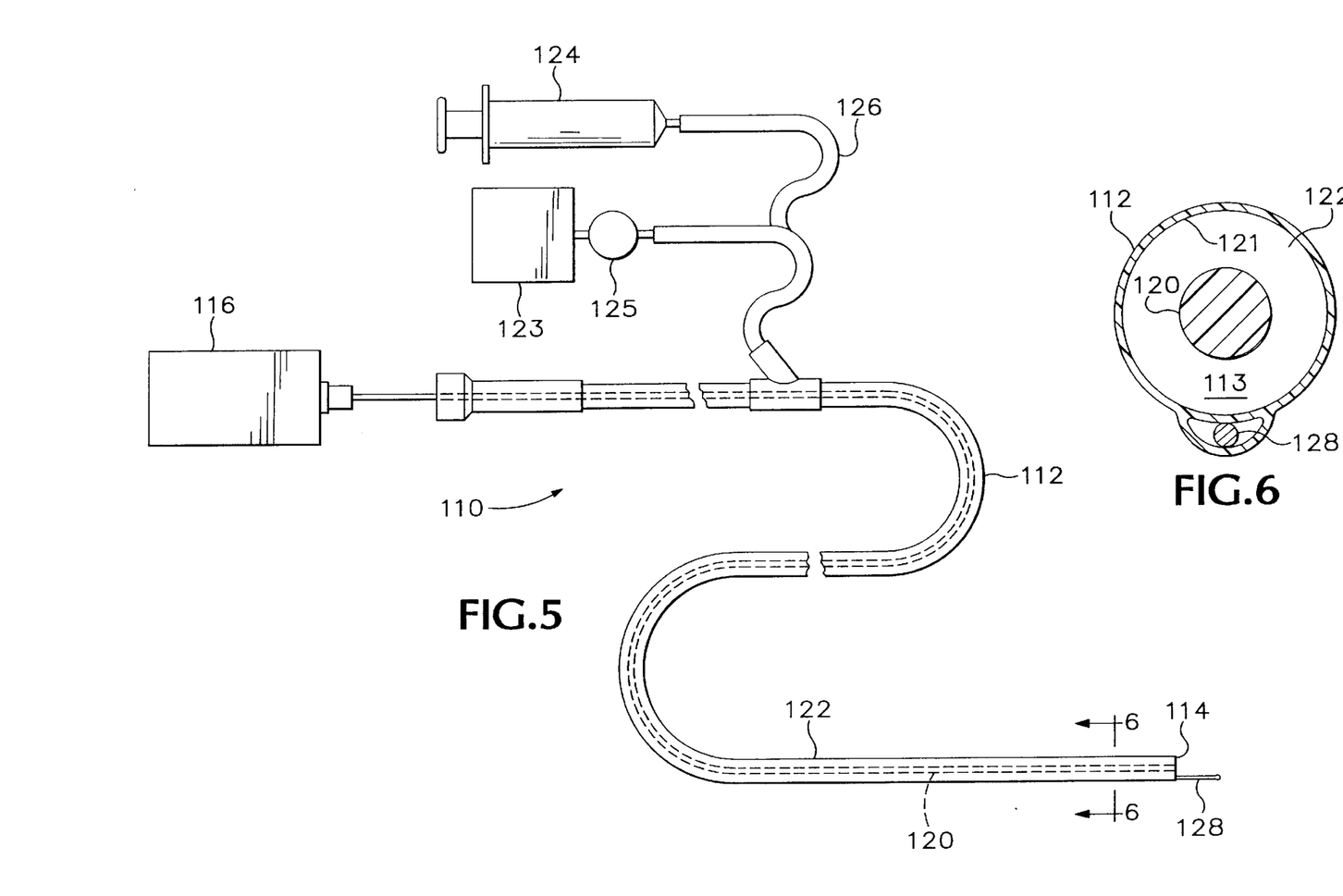
FIG. 5 is a schematic diagram of a preferred embodiment according to the present invention.
FIG. 6 is a cross-sectional view taken along 6—6 of FIG. 5.
Figure 7:
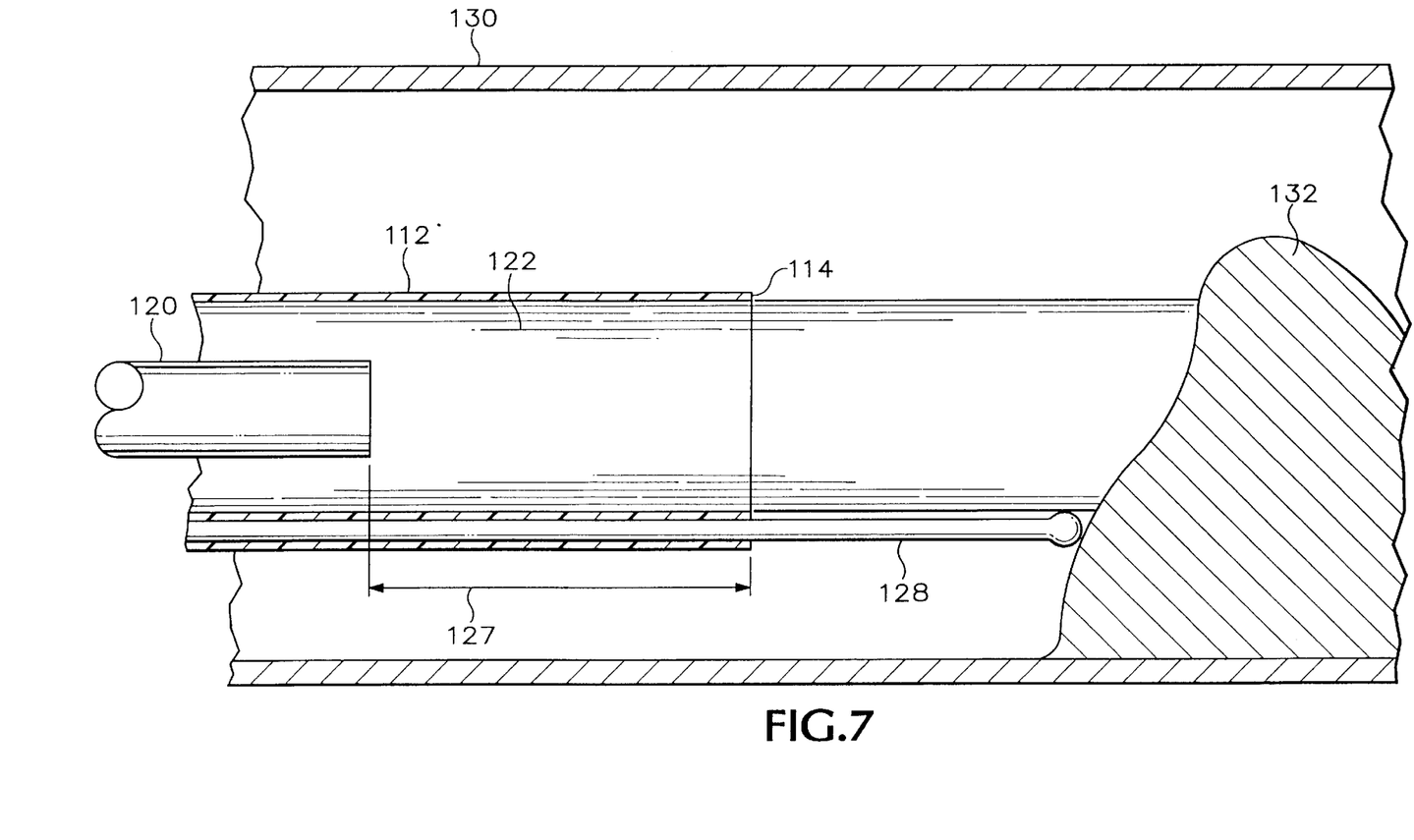
FIG. 7 is a lengthwise sectional view of the distal end portion of the embodiment of FIG. 5, shown in an arterial lumen in proximity to a blood clot.
Figure 8:
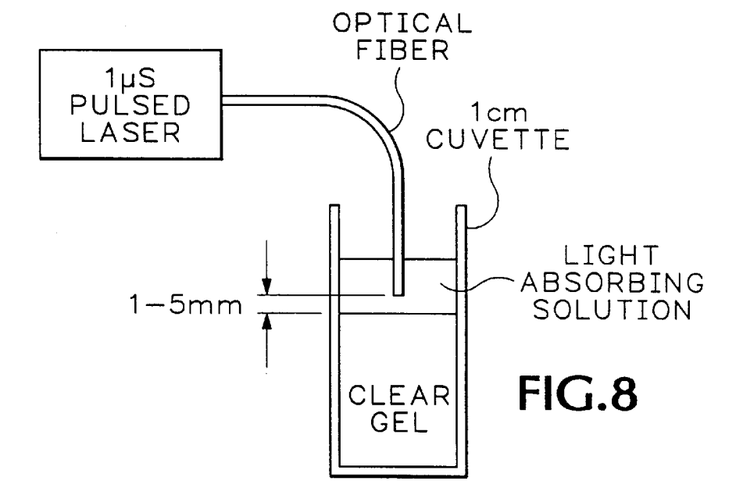
FIG. 8 is a schematic diagram showing the experimental setup used to test the characteristics of Photoacoustic Drug Delivery (PADD).
Figure 9:
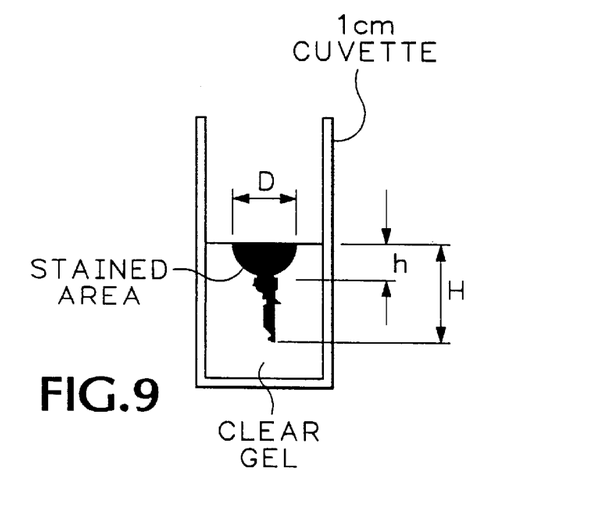
FIG. 9 is a cross-sectioned representation of dye delivery to a target from the experimental setup shown in FIG. 8.

FIGS. 5–7 illustrate a preferred embodiment according to the present invention. In referring to FIGS. 5–7, I now describe a liquid core laser with particular reference to its use in locally delivering a drug during angioplasty. The invention has particular utility in ablating and pharmacologically treating ablating obstructions such as atheromatous plaque, an atheroembolus, thrombus, and blood clots.

FIG. 5 illustrates a system 110 that employs the liquid core laser drug delivery system of the present invention. System 110 is very similar to system 10 as I described above except that it has the additional advantage of delivering laser energy via a liquid core of light transmissive liquid 113 to a selected site. The advantages of using a liquid core laser is discussed by Gregory et al. in their article *"Liquid Core Light Guide for Laser Angioplasty", IEEE Journal of Quantum Electronics.* Vol 26, No. 12, December 1990, which is fully incorporated herein by reference for all purposes. System 110 includes a catheter 112 having a flexible distal end 114 for insertion into the lumen 134. A guidewire 128 guides the distal end to the site 132. The catheter 114 encloses a conduit 122 which is filled with a liquid having a suitable index of refraction. The conduit's sidewall defines a lumenal surface and has a suitably low index of refraction compared to the light transmissive fluid to allow internal reflection of light through which the liquid flows.

Once I have positioned the distal end 114 adjacent the site 132, I introduce light transmissive liquid 113 at the proximal end of the conduit 122 from a liquid source 123. Liquid discharge means 125, such as an injector pump or syringe, discharges the liquid 113 into the conduit 122. I then direct and couple laser energy from a source of laser energy 116 into the proximal end of optical fiber 120. Optical fiber 120 launches the laser energy into the liquid 113. Alternately, syringe 124 and liquid source 123 can be the same reservoir. The energy passes within the liquid filled conduit 122 toward distal end 114. The energy is attenuated as it passes away from the energy source 116, so that a portion of it emerges from the distal end 114. The proportion of the energy introduced into the liquid 113 that emerges from the distal end 114 of the liquid filled conduit 122 depends upon the dimensions and physical characteristics of the liquid and upon the conduit side wall, and on the extent to which the catheter 112 follows a curving course.

I select materials for sidewall 121 and for liquid 113 based in part to provide a high degree of internal reflection at the conduit surface. Specifically, wall 121 and liquid 113 are each transparent to laser energy which is conducted through the conduit while the index of refraction $N_w$ of wall 121 is less than the index of refraction of $N_f$ of liquid 113. Further, I select material for wall 121 in part to provide structural strength as well as flexibility so that the liquid-filled conduit can be bent through curves of small radius without kinking or substantially distorting the cross sectional geometry of the conduit 122. I prefer to make sidewall 121 out of a fluorinated ethylenepropylene which is available commercially, for example as "FEP Teflon®" or a coating of a suitably low index of refraction optical media or alternatively a reflective surface such as metalized gold or silver coating.

The light transmissive liquid 113 is injectable, transparent in laser wavelengths, and has a refractive index greater than the refractive index of sidewall 121. Suitable liquids include solutions of sugars such as mannitol, glucose, dextrose, and iodinated contrast media. I prefer a solution having a refractive index of about 1.4. For example, FEP Teflon® has a refractive index of about 1.33, thus, the ratio of refractive indices relative to such solutions is approximately 1.1. A ratio of 1.1 provides for substantially total internal reflection even at fairly steep angles of incidence. I prefer that the surface of sidewall 121 be smooth because if it is not, surface roughness can produce unsatisfactory irregularities in angle of incidence.

The thickness of the sidewall 121 is generally less than 0.010 inches. A conduit that is 110 cm long, has an interior sidewall of FEP Teflon® and contains a sugar solution, can transmit about 60% of the laser energy at 480 nm to the distal end which is launched through a refractive index-matched lens or window into the proximal end from a laser. I prefer to launch laser energy from the optical fiber 120 into the fluid stream at a distance 127 ranging from the tip of catheter 112 to a position about 20 cm withdrawn from the distal end 114.

The diameter of catheter 112 is about 0.3–3 mm depending upon the diameter of the body lumen 130. Some materials that are optically suitable for use as a catheter sidewall are structurally unsuitable or less suitable because they are insufficiently flexible, or they collapse or kink or otherwise are distorted when they are bent through curves of small radius.

The liquid core laser delivery system 110 operates generally as follows, with specific reference to its use for ablating and pharmacologically treating coronary arteries occluded by arterial plaque. I fill conduit 122 with liquid 113, and then couple a source 123 of liquid to the proximal end of conduit 122. I then introduce the liquid-filled conduit 122, distal end first through an opening in the skin and through the wall of a large artery such as the femoral artery, and then direct the catheter toward the selected site 132, until the distal end 114 is directed toward the occlusion.

Once the distal tip has reached the site 132, I introduce a further quantity of liquid into the conduit from the liquid source 123, causing some liquid to emerge from the distal end of the tube toward the site. Optionally, the flow of liquid from the distal end can be deflected towards the selected site using a deflectable tip. Devices which provide a deflectable tip as by torsional rotation means, such as Sones or Judkins catheters, are well known in the art. Next, I introduce the active agent in solution into the stream of flowing liquid 113.

For instance, I would locally deliver cell toxins to treat cancerous tumors or other growths.

When the active agent, carried by the flowing liquid reaches the selected site 132, I energize laser 116. The timing of the laser energizing depends upon several variables including the distance between the point of introducing the active agent into the liquid core to the distal end of the catheter and the flow rate of the flowing liquid. The object is to wait until the active agent is in the vicinity of the selected site before I energize the laser. For example, if the distance between the source of active agent and the distal end is 50 cm and the flow rate at which the flowing liquid travels through the catheter is 2 cm/sec., then I would energize the laser 25 seconds after the active agent solution was introduced into the liquid core. For effective delivery of the active agent to the site, I prefer to use a light transmissive liquid flow rate of about 0.1 to 1.0 cc/sec. and most prefer a flow rate of about 0.3 cc/sec.

When I energize laser 116, it sends a pulse of laser energy along liquid core 113. I prefer using an energy pulse which has an amplitude ranging from about 400 to 600 nm; and most prefer an energy pulse ranging from about 480 to 580 nm for treatment of thrombus. One can then achieve a vaporization event which would then drive the active agent located in the ambient fluid around the site of the vaporization by absorption of the laser energy by some local target such as hemoglobin at selected site 132. The most likely application of this technology would be in the thrombus. Laser energy could then be transported to the target via fluid core light guides or simply by conventional fused silica fiber(s) whole distal tip could be located anywhere from inside the distal end 114 of fluid transport conduit 122 to out in the lumen 130.

In another aspect of the invention, a light absorptive liquid is introduced into conduit 122 which absorbs the laser light substantially adjacent the distal tip of the optical fiber 120. In this case, only conventional fiber optics could be used instead of waveguiding liquid wherein the distance 127 between the distal tips of the catheter 112 and optical fiber 120 is approximately zero (see, for instance, the system shown in FIG. 3). Alternately, the distal tip of the optical fiber can extend beyond the tip of the catheter and into the lumen 130. The drug fluid 113 would also be the laser absorptive media and detonating or vaporizing this fluid would produce the vapor bubble and then displacement which would drive the drug into the local tissues, such as at selected site 132. An example of an absorptive liquid would be saline or water in combination with a Holmium laser which emits wavelengths in the infra-red between 1900 and 2100 nm, wavelengths which are highly absorbed by water. Firing this laser on water or saline would create the bubble, preferably originating from between about 0.01 millimeters and 10 millimeters spaced from the site, for driving a drug into the tissues. This particular method can be useful so long as the drug itself is not absoptive of the particular wavelength of light used.

EXAMPLE

Laser Delivery

A 1 $\mu$s pulsed dye laser (Palomar Medical Technologies) operating at a wavelengths of 480–577 nanometers was used in this study. The laser energies varied from 30–100 millijoules. The repetition rate ranged from 1–10 hertz. Pulse-to-pulse energy variation was less than 5%. Optical fibers of 300, 600, and 1000 micron core diameter were used to deliver the laser pulses into the light absorbing solution.

Preparation of Thrombus Models

The thrombus was modeled using 3.5% gelatin (60–300 bloom). The strength of the gelatin was proportional to the bloom number. The gelatin-water mixture was heated to 60° C. with stirring until it became clear. Liquid gelatin samples were poured into 1 centimeter cuvettes and cured to form 1–1.5 centimeter thick tissue models.

Preparation of Light Absorbing Solutions

Solutions of a hydrophobic dye (D&C Red #17 Warner-Jenkinson Co., Inc.) in mineral oil (Paddock Laboratories, Inc.) were used as a model for the drug. The hydrophobic dye was used to detect delivered drug in clear gelatin because the gels were water-based and staining of the surface was undesirable. The dye was added to the mineral oil to achieve the desired absorption coefficient. The absorption coefficients of the solutions had a nearly linear relationship with the concentration of the dye in the oil: 0.0367 grams of dye in 30 milliliter oil gave an absorption coefficient of 300 $cm^{-1}$ at 504 nm. The absorption coefficients in our experiments varied from 50 to 300 $cm^{-1}$. The dye-oil mixture was heated to 100° C. with stirring until the appearance became uniform, and then cooled down to room temperature. The solution of 300 $cm^{-1}$ was easy to saturate at room temperature. Usually, after 4 hours the dye began to precipitate, and the absorption coefficient was dropped to 250 $cm^{-1}$.

Procedures of Photoacoustic Drug Delivery

The experimental setup is outlined in FIG. 8. The light absorbing solution was drawn up into a 1 cm cuvette ~1.5 cm on top of the clear gelatin. The cuvette was fixed with a heavy clamp to prevent displacement caused by the violent vibration associated with some laser-induced acoustic transients. Ten laser pulses were delivered through a solid glass fiber into the solution for each ablation except for the study on the effect of pulse numbers on the delivery (in this case, 10–100 pulses were delivered). The fiber tip was located 1–5 mm above the surface of the gel samples. The cavitation bubbles were formed at the fiber tip. The laser energy output was measured with a joulemeter (J50LP, Molectron Detector, Inc.) before and after each ablation. Following photoacoustic drug delivery, the samples were sectioned and measured with a stereo optical microscope (SZ6045, Olympus). The stained areas in the clear gels indicated the presence of photoacoustically delivered dye. FIG. 9 shows how the spatial distributions of delivered drug in the gelatin were measured. The stained areas consisted of two parts: an inverted hemisphere with a diameter D and height h inserted on the surface of the gel, and some colored cracks below the hemisphere having a total height H.

RESULTS

In these experiments, the spatial distribution of dye in clear gel samples with spatially unconfined geometry was measured. I have found that while the dye can be driven a few millimeters into the gels in both axial (i.e., H and h) or radial (i.e., D) directions, the penetration was less than 500 microns when the gel surface remained macroscopically undamaged. The following Tables 1–7 present the results for the effects of target material, laser energy, absorption coefficient, fiber size, repetition rate, and number of pulses on the spatial distribution of delivered drug.

Spatial Distribution of Drug in Axial Direction

According to the experimental data, the penetration of a drug in the axial direction increases with increasing the laser energy, absorption coefficient, and pulse number, shown in Tables 2, 3, and 6. The penetration is reduced for greater strength, larger fibers, and increased distance between the fiber tip and the gel surface increase (Tables 1, 4, and 7). The data is inconclusive whether repetition rate would affect the spatial distribution of delivered dye in actual tissue, cf., Table 5. During the ablation, it was found that the dye was easily driven into the low strength gel samples. For example, the dye was driven into the weaker gel (60 bloom) after one or two pulses, while at least five pulses were needed to push the dye into the stronger gel samples (300 bloom). With increasing laser energy and absorption coefficient, a popping sound became louder due to the cavitation bubble collapse.

Spatial Distribution of Drug in Radial Direction

As indicated by the data, the penetration of a drug in the radial direction may be relatively independent of the laser energy, absorption coefficient, and repetition rate, but it is reduced as the strength of the gels increases. Table 6 shows that the penetration increases significantly when the number of pulses increases. The variation in the penetration is also large when the fiber size changes. I observed that during the ablation with a 300 micron fiber, the solution was explosively ejected and the solution in front of the fiber tip became dark, i.e., it was burnt. The ablation using a 600 micron fiber was more violent than that using a 1000 micron fiber, but no explosive ejection was observed.

EXPERIMENT 1

Effect of Target Material Strength

Penetration of dye in clear gel was plotted against the gel mechanical strength. A light absorbing solution having an absorption coefficient of 300 $cm^{-1}$ was used. Ten pulses of 60 mJ laser energy at 3 Hz were delivered through a 1000 micron diameter fiber. A 3.5% gelatin (60 bloom, 175 bloom, 300 bloom) was used as the target. The fiber was located 1 mm above the gel surface.

TABLE 1

| | Diameter (D) | Crack Height (H) | Axial Height (h) |
| --- | --- | --- | --- |
| 60 $cm^{-1}$ bloom | 2.1 mm | 0.8 mm | 0.25 mm |
| 175 $cm^{-1}$ bloom | 2.0 mm | 0.3 mm | 0.15 mm |
| 300 $cm^{-1}$ bloom | 1.4 mm | 0.2 mm | 0.10 mm |

EXPERIMENT 2

Effect of Laser Energy

Penetration of dye in clear gel was measured as a function of the laser pulse energy. A light absorbing solution having an absorption coefficient of 300 $cm^{-1}$ was used. Ten pulses of the laser energies (30 mJ, 60 mJ, 100 mJ) at 3 Hz were delivered through a 1000 micron diameter fiber. A 3.5% gelatin (175 bloom) was used as the target. The fiber was located 1 mm above the gel surface.

TABLE 2

| | Diameter (D) | Crack Height (H) | Axial Height (h) |
| --- | --- | --- | --- |
| 30 mJ | 2.2 mm | ~0 mm | 0.05 mm |
| 60 mJ | 2.0 mm | 0.2 mm | 0.15 mm |
| 100 mJ | 2.3 mm | 0.3 mm | 0.2 mm |

EXPERIMENT 3

Effect of Absorption Coefficient of Liquid

The penetration of dye in clear gel was measure as a function of the absorption coefficient of the light absorptive liquid. Absorption coefficients of the light absorptive liquid tested were 50 $cm^{-1}$, 100 $cm^{-1}$, and 300 $cm^{-1}$. Ten pulses of 60 mJ laser energy at 3 Hz were delivered through a 1000 micron diameter fiber. A 3.5% gelatin (175 bloom) was used as the target. The fiber was located 1 mm above the gel surface.

TABLE 3

| | Diameter (D) | Crack Height (H) | Axial Height (h) |
| --- | --- | --- | --- |
| 50 $cm^{-1}$ | 1.9 mm | ~0 mm | 0.05 mm |
| 100 $cm^{-1}$ | 2.2 mm | ~0 mm | 0.10 mm |
| 300 $cm^{-1}$ | 2.05 mm | 0.35 mm | 0.15 mm |

EXPERIMENT 4

Effect of Fiber Size

The penetration of dye in clear gel was measured as a function of fiber size. The absorption coefficient was 300 $cm^{-1}$. Ten pulses of 60 mJ laser energy at 3 Hz were delivered through optical fibers having diameters of 300 micron, 600 micron, and 1000 micron. A 3.5% gelatin (175 bloom) was used as the target. The fibers were located 1 mm above the gel surface.

TABLE 4

| | Diameter (D) | Crack Height (H) | Axial Height (h) |
| --- | --- | --- | --- |
| 300 $\mu m$ | 3.2 mm | 1.0 mm | 0.20 mm |
| 600 $\mu m$ | 1.55 mm | 0.25 mm | 0.175 mm |
| 1000 $\mu m$ | 2.0 mm | 0.20 mm | 0.15 mm |

EXPERIMENT 5

Effect of Repetition Rate

The penetration of dye in clear gel was measured as a function of repetition rate. The absorption coefficient was 300 $cm^{-1}$. Ten pulses of 60 mJ laser energy operating at 1–10 Hz were delivered through a 1000 micron diameter fiber. A 3.5% gelatin (175 bloom) was used as the target. The fiber was located 1 mm above the gel surface.

TABLE 5

| | Diameter (D) | Crack Height (H) | Axial Height (h) |
| --- | --- | --- | --- |
| 1 hertz | 1.8 mm | 0.1 mm | 0.15 mm |
| 2 hertz | 1.7 mm | ~0 mm | 0.15 mm |
| 3 hertz | 2.0 mm | 0.1 mm | 0.15 mm |
| 5 hertz | 1.8 mm | ~0 mm | 0.15 mm |
| 7 hertz | 2.1 mm | 0.25 mm | 0.15 mm |
| 10 hertz | 1.9 mm | ~0 mm | 0.15 mm |

EXPERIMENT 6

Effect of Pulse Number

The penetration of dye in clear gel was measured as a function of the number of laser pulses used. The absorption coefficient was 300 $cm^{-1}$. A total of 10–100 pulses of 60 mJ laser energy at 3 Hz were delivered through a 1000 micron diameter fiber. A 3.5% gelatin (175 bloom) was used as the target. The fiber was located 1 mm above the gel surface.

TABLE 6

|  | Diameter (D) | Crack Height (H) | Axial Height (h) |
| --- | --- | --- | --- |
| 10 pulses | 1.4 mm | ~0 mm | 0.15 mm |
| 20 pulses | 2.05 mm | 0.35 mm | 0.175 mm |
| 30 pulses | 2.25 mm | 0.45 mm | 0.20 mm |
| 50 pulses | 2.4 mm | 0.95 mm | 0.25 mm |
| 100 pulses | 2.8 mm | 2.0 mm | 0.50 mm |

EXPERIMENT 7

Effect of Fiber Distance from Target

The penetration of dye in clear gel was measured as a function of the distance between the fiber tip and the target gel surface. The absorption coefficient was 300 cm$^{-1}$. Ten pulses of 60 mJ laser energy at 3 Hz were delivered through a 1000 micron diameter fiber. A 3.5% gelatin (175 bloom) was used as the target. The fiber was located 1–5 mm above the gel surface.

TABLE 7

|  | Diameter (D) | Crack Height (H) | Axial Height (h) |
| --- | --- | --- | --- |
| 1 mm | 1.3 mm | 0.075 mm | 0.15 mm |
| 2 mm | 1.7 mm | 0.10 mm | 0.125 mm |
| 3 mm | 1.6 mm | ~0 mm | 0.10 mm |
| 4 mm | 1.7 mm | ~0 mm | 0.10 mm |
| 5 mm | 0.8 mm | ~0 mm | 0.05 mm |

DISCUSSION

The aim of these experiments were to model the mechanisms of Photoacoustic Drug Delivery (PADD) which would drive clot-dissolving enzymes, for instance, into clots or vessel walls to enhance the efficiency of laser thrombolysis. The effects of the laser parameters on the spatial distribution of delivered drug using a gelatin-based thrombus model were investigated. The experiments measure the spatial distribution of delivered dye in clear gel samples. Normally, deeper penetration was accompanied by louder popping sounds.

The pulse number affects the penetration significantly. In a comparison of Table 6 with Table 2, we find that a similar delivery can be achieved by using 60 mJ laser energy delivered by a 1000 micron fiber and 10 additional pulses instead of using 100 mJ laser energy. This suggests that a similar delivery may be achieved by using lower energy with increasing pulse number, rather than using higher energy.

In these experiments, I have demonstrated that laser-induced acoustic pressure can be used to drive drug into tissue, and identified the mechanisms of PADD. Several conclusions can be drawn from these experiments:

The penetration of dye in gel is proportional to the laser energy, absorption coefficient, and pulse number.

Increasing the strength of the material and the distance between the fiber tip and the target surface reduces the extent of the delivery.

While the dye can be driven a few millimeters into the gel in both the axial and radial direction, the penetration is less than 500 microns when the gel surface remains macroscopically undamaged.

The penetration mainly depends on the radiant exposure.

Similar delivery can be achieved by using less energy through a smaller fiber or with additional pulses.

While the preceding data validates the concept of PADD, those experienced in the practice of medicine recognize that gelatins are not necessarily an accurate model of thrombus or tissue in general. Therefore, the parameters for maximizing PADD in geletin may not be entirely accurate for predicting effective parameters for treatment in patients. Accordingly, it is anticipated that the preferred number of laser energy pulses used are between about 1 and 1000, that the preferred diameter of the optical fiber used to transmit the energy pulses is between about 100 and 1000 micrometers, that the preferred range of energy of the laser pulse is between about 2 and 800 millijoules, and that the preferred coefficient of absorption of the light absorptive liquid used is between about 50 and 800 cm$^{-1}$.

While the above experiments illustrated the mechanisms which affected photoacoustic drug delivery (PADD), another experiment performed on real tissue demonstrated the advantages of PADD over other drug delivery methods such as infusion. In the experiment, 10 thrombosed porcine carotid arteries were treated. The agent used in the experiment comprised 1 µm fluorescent microspheres (agent) prepared in a solution of 1×10$^7$ microspheres per cc. A 1.0 mm laser ablated channel was created in each 5.0 mm diameter vessel with a single pass of a fluid core optical catheter (OC)—a 1 mm diameter teflon tube fitted with a 300 µm optical fiber coupled to a 2 µs pulsed dye laser emitting 577 nm light at 50 mJ/pulse. Saline flowing through the OC carried light and agent to the thrombus. Five of the treatment vessels received PADD: laser energy and simultaneous delivery of agent solution at 4 cc/min via the OC. Five of the arteries were infused with 1 µm fluorescent microspheres in solution for a similar time after the laser channel was created. Frozen sections were viewed under light and fluorescence microscopy. Areas and depth of MS penetration into thrombus were measured. An optical multichannel analyzer measured fluorescence intensity, normalized per the microspheres. The following table shows the results obtained:

TABLE 8

|  | PADD | Infusion |
| --- | --- | --- |
| Penetration Area (p = 0.02) | 0.13 ± 0.02 mm$^2$ | 0.020 ± 0.004 mm$^2$ |
| Maximum Depth (p = 0.01) | 327 ± 36 µm | 173 ± 33 µm |
| Microspheres/Sample (p = 0.0002) | 366 ± 63 | 164 ± 20 |

It was found that the mean agent penetration area and max depth of agent into the thrombus were greater in PADD vessels. Additionally, the number of microspheres found in each sample was higher in PADD vessels. Thus, it appears that PADD can increase local delivery of agent to arterial thrombi compared to infusion alone.

Although I have specifically described preferred embodiments and methods, I contemplate that various modifications could be made without deviating from the spirit of the present invention. For example, the present invention could be used to: drive vasorelaxants into vessels prone to spasm; drive growth factor antagonists into vessel walls to prevent atherogenesis; implement cross linking agents during laser welding or cauterizing procedures; implant liposomes into lumenal surfaces; and drive dyes and other biological and gene products into blood vessel walls.

Having described and illustrated the principles of the invention in a preferred embodiment thereof, it should be apparent that the invention can be modified in arrangement and detail without departing from such principles. I claim all modifications and variation coming within the spirit and scope of the following claims.

I claim:

1. A method for locally delivering an active agent to a selected site in a body lumen containing an ambient body fluid using a catheter, the catheter including a flexible distal end for insertion into the lumen, the method comprising the steps of:

preparing a solution of the active agent;

inserting the flexible distal end of the catheter into the lumen;

directing the flexible distal end adjacent the selected site;

introducing the active agent solution adjacent the selected site; and transmitting laser energy from an energy generating source to the site via the catheter, with an amplitude sufficient to create a hydraulic or pressure wave which drives the active agent into the site.

2. The method of claim 1 wherein the catheter includes a conduit housed within the catheter, the method further including:

introducing a flow of the active agent solution into the conduit for discharge at the distal end into the lumen adjacent the site.

3. The method of claim 2 wherein the active agent solution introduced adjacent the selected site is optically transparent to the laser energy transmitted to the site via the catheter.

4. The method of claim 3 wherein the active agent solution introduced adjacent the selected site is light transmissive, the method further including:

directing the laser energy transmitted via the catheter through the light transmissive solution to the site so as to create a hydraulic wave at the site, the conduit having a sidewall capable of reflecting light into the light transmissive solution in the conduit so that the liquid waveguides the laser energy through the conduit to the selected site.

5. The method of claim 4 wherein the flowing liquid has an index of refraction greater than the index of refraction of the sidewall.

6. The method of claim 5 wherein the liquid has an index of refraction of about 1.4 and sidewall has an index of refraction of about 1.3.

7. The method of claim 4 wherein the sidewall includes a metalized surface capable of reflecting light.

8. The method of claim 2 wherein the active agent solution introduced adjacent the selected site is absorptive of the laser energy so as to create a hydraulic or pressure wave which originates at a location spaced from the selected site.

9. The method of claim 8 wherein the origin of the hydraulic wave is spaced from between about 0.01 and 10 millimeters from the site.

10. The method of claim 8 wherein the catheter includes an optical fiber of a certain diameter housed within the catheter, the method further including:

coupling the optical fiber to the external laser source; and transmitting the laser energy through the fiber.

11. The method of claim 10 wherein the diameter of the optical fiber is between about 100 and 1000 micrometers.

12. The method of claim 8 wherein the catheter includes a plurality of bundled optical fibers of certain diameteres housed within the catheter, the method further including:

coupling the optical fiber bundle to the external laser source; and transmitting the laser energy through the fiber.

13. The method of claim 12 wherein the diameter of the each of the optical fibers in the bundle are between about 30 and 300 micrometers.

14. The method of claim 1 further including transmitting a predetermined number of laser energy pulses to the site via the catheter.

15. The method of claim 14 wherein the predetermined number of laser energy pulses transmitted to the site via the catheter is between about 1 and 1000.

16. The method for delivering an active agent to a selected site of claim 1, further including selecting an laser energy source from a set of parameters consisting of laser energy, number of pulses, catheter size, distance between catheter tip and selected site, absorption coefficient of the target and tissue strength of the target area at the selected site.

17. The method of claim 1 wherein the lumen is selected from the group consisting of an artery, a vein, a ureter, a common bile duct, a trachea, a bronchus, and a gastrointestinal tract.

18. The method of claim 1 wherein the site is selected from the group consisting of an atheromatous plaque, an atheroembolus, a thrombus, a blood clot, a lesion, a kidney stone, a gall stone, a tumor, and a polyp.

19. The method of claim 1 wherein the site is selected from the group consisting of an atheromatous plaque, an atheroembolus, a thrombus, and a blood clot; and the active agent is selected from the group consisting of one or more of streptokinase, urokinase, recombinant tissue plasminogen activator and heparin.

20. A system for locally delivering an active agent to a selected site in a body lumen containing ambient body fluid, the system comprising:

a source of the active agent in solution;

a flexible tube having a distal end for insertion into the lumen;

a conduit in the flexible tube, coupled to the source of the active agent, for delivering the active agent to the site; and means for transmitting laser energy to the site in a pulse of sufficient amplitude to create a hydraulic or pressure wave which drives the active agent into the selected site.

21. The catheter of claim 20 wherein the flexible tube is sized to fit a body lumen selected from the group consisting of an artery, a vein, a ureter, a common bile duct, a trachea, a bronchus, and a gastrointestinal tract.

22. The catheter of claim 20 further comprising a guidewire disposed at the distal end of the tube.

23. The catheter of claim 20 wherein the means for transmitting energy includes an optical fiber.

24. The system of claim 20 wherein the energy transmitting means comprises:

a source of laser energy capable of transmitting a pulse of energy of between about 2 and 800 millijoules.

25. The system of claim 20 wherein the energy transmitting means comprises:

a source of laser energy; and an optical fiber coupled to the source of laser energy, housed within the tube, capable of transmitting laser energy from the source of laser energy to the site.

26. The system of claim 25 wherein the optical fiber has a diameter of between about 100 and 1000 micrometers.

27. The system of claim 25 wherein the solution includes a light absorptive liquid.

28. The system of claim 27 wherein the light absorptive liquid has an absorption coefficient of between about 50 and 800 $cm^{-1}$.

29. The system of claim 25 were in the optical fiber includes a distal tip which is at or extends beyond the distal end of the flexible tube into the lumen.

30. The system of claim 20 wherein the solution includes a light transmissive liquid, the energy transmission means comprising:
a source of laser energy, the conduit being coupled to the source of laser energy and having a conduit sidewall capable of reflecting light into the solution in the conduit so that the liquid waveguides the laser energy through the conduit to the selected site.

31. The catheter of claim 30 wherein the light transmissive liquid has an index of refraction greater than the index of refraction of the sidewall.

32. The catheter of claim 31 wherein the liquid has an index of refraction of about 1.4 and sidewall has an index of refraction of about 1.3.

33. The catheter of claim 30 wherein the light transmissive liquid is injectable and transparent in laser wavelengths.

34. The catheter of claim 33 wherein the liquid is selected from the group consisting of one or more of mannitol, glucose, dextrose and iodinated contrast medium.

35. The system of claim 20 wherein the energy transmitting means comprises:

a source of laser energy; and a plurality of optical fibers coupled to the source of laser energy, housed within the tube, capable of transmitting laser energy from the source of laser energy to the site.

36. The system of claim 35 wherein the optical fibers each have a diameter of between 30 and 300 micrometers.

* * * * *